United States Patent
Murao et al.

(10) Patent No.: US 7,749,739 B2
(45) Date of Patent: Jul. 6, 2010

(54) PROCESS FOR PRODUCING AMIDE COMPOUND USING MICROBIAL CATALYST

(75) Inventors: Kozo Murao, Kanagawa (JP); Katsuo Ishii, Kanagawa (JP)

(73) Assignee: Dia-Nitrix Co., Ltd., Tokyo (JP)

(*) Notice: Subject to any disclaimer, the term of this patent is extended or adjusted under 35 U.S.C. 154(b) by 832 days.

(21) Appl. No.: 10/450,532

(22) PCT Filed: Dec. 19, 2001

(86) PCT No.: PCT/JP01/11149

§ 371 (c)(1),
(2), (4) Date: Jun. 20, 2003

(87) PCT Pub. No.: WO02/50297

PCT Pub. Date: Jun. 27, 2002

(65) Prior Publication Data

US 2004/0048348 A1    Mar. 11, 2004

(30) Foreign Application Priority Data

Dec. 20, 2000 (JP) ............................. 2000-387537

(51) Int. Cl.
*C12P 13/02* (2006.01)
(52) U.S. Cl. .................. 435/129; 435/170; 435/243; 435/253.3
(58) Field of Classification Search ........ 435/129, 435/219, 170, 243, 253.3
See application file for complete search history.

(56) References Cited

U.S. PATENT DOCUMENTS

| | | | |
|---|---|---|---|
| 4,001,081 A | | 1/1977 | Commeyras et al. |
| 4,248,968 A | | 2/1981 | Watanabe et al. |
| 5,318,908 A | | 6/1994 | Seki et al. |
| 5,334,519 A | * | 8/1994 | Yamada et al. ............. 435/129 |
| 5,654,180 A | * | 8/1997 | Beppu et al. ............... 435/129 |
| 5,731,176 A | * | 3/1998 | Yamada et al. ............. 435/129 |
| 5,827,699 A | * | 10/1998 | Yanenko et al. ............ 435/129 |
| 5,866,379 A | * | 2/1999 | Burlingame et al. ........ 435/129 |
| 6,133,478 A | * | 10/2000 | Parkins et al. .............. 564/126 |

FOREIGN PATENT DOCUMENTS

| | | |
|---|---|---|
| CN | 1054614 A | 9/1991 |
| CN | 1070686 A | 4/1993 |
| EP | 93782 | 11/1983 |
| EP | 188316 | 7/1986 |
| EP | 204555 | 12/1986 |
| EP | 307926 | 3/1989 |
| EP | 0 444 639 A2 | 9/1991 |
| EP | 445646 | 9/1991 |
| EP | 0 530 522 A2 | 3/1993 |
| EP | 790310 | 8/1997 |
| JP | 02-177883 | 10/1990 |
| JP | 6-225780 | 8/1994 |
| JP | 8-266277 | 10/1996 |
| JP | 2002-551176 | 5/2005 |

OTHER PUBLICATIONS

Nagasawa et al. "Characterization of a new cobalt-containing nitrile hydratase . . . " Eur. J. Biochem. (1991) 196:581-589.*
Nagasawa, T., et al., "The Superiority of the Third-Generation Catalyst, Rhodococcus Rhodochrous J1 Nitrile Hydratase, for Industrial Production of Acrylamide," Appl. Microbiol Biotechnol, 40, pp. 189-195, 1993.
U.S. Appl. No. 11/813,376, filed Jul. 5, 2007, Ishii, et al.

* cited by examiner

*Primary Examiner*—Irene Marx
*Assistant Examiner*—Susan Hanley
(74) *Attorney, Agent, or Firm*—Oblon, Spivak, McClelland, Maier & Neustadt, L.L.P.

(57) ABSTRACT

This invention relates to a process for producing an amide compound from a nitrile compound using a microbial catalyst, wherein a microbial cell having nitrile hydratase activity of 50 U or higher per mg of dry cell at a reaction temperature of 10° C. is brought into contact with a nitrile compound in an aqueous medium without being immobilized. This method utilizes a microbial cell that exhibits high nitrile hydratase activity in the reaction without being entrap-immobilized. Thus, an amide compound can be effectively produced from a nitrile compound without problems of decreased reaction speed or lowered amount produced per unit cell amount, which are caused by entrap-immobilization. Accordingly, an amide compound can be produced within a very short period of time in the case of a batch reaction and with a very small-scale facility in the case of a continuous reaction.

4 Claims, No Drawings

US 7,749,739 B2

PROCESS FOR PRODUCING AMIDE COMPOUND USING MICROBIAL CATALYST

This application is a national stage entry of PCT/JP01/11149, filed Dec. 19, 2001 which claims priority to Japanese Application No. 2000-387537, filed Dec. 20, 2000.

TECHNICAL FIELD

The present invention relates to a process for producing an amide compound from a nitrile compound using a microorganism having nitrile hydratase activity.

BACKGROUND ART

Recently, a process for synthesizing a compound using a biocatalyst has been used for producing a variety of compounds because of advantages such as moderate reaction conditions, simplified reaction processes, and high purity of reaction products due to small amounts of by-products.

Since the discovery of nitrile hydratase, an enzyme that converts a nitrile compound into an amide compound, biocatalyst utilization has been actively studied in the production of amide compounds (JP Patent Publication (Kokai) No. 11-123098, JP Patent Publication (Kokai) No. 7-265091, JP Patent Publication (Kokoku) No. 56-38118, and JP Patent Publication (Kokai) No. 11-89575).

At present, a microorganism having nitrile hydratase activity is used for producing acrylamide, nicotineamide, or the like at the industrial level for a superior reaction process from the viewpoints of operability, safety, economic efficiency, and other factors.

Up to the present, a considerable number of microorganisms have been found having nitrile hydratase activities. Examples thereof include microorganisms belonging to the genera *Nocardia, Corynebacterium, Bacillus, Pseudomonas, Micrococcus, Rhodococcus, Acinetobacter, Xanthobacter, Streptomyces, Rhizobium, Klebsiella, Enterobacter, Erwinia, Aeromonas, Citrobacter, Achromobacter, Agrobacterium,* and *Pseudonocardia.*

Among them, the genera *Pseudomonas, Bacillus, Rhodococcus,* and *Pseudonocardia* express a nitrile hydratase having a very high level of activity and stability. Thus, they are used at the industrial level or levels similar thereto.

Further, when culturing these microorganisms, it is known that a microbial cell having highly active nitrile hydratase is obtained by a method of adding nitriles or amides (JP Patent Publication (Kokoku) Nos. 61-43996 and 61-43999), a method of adding amino acid (JP Patent Publication (Kokoku) Nos. 61-43997 and 61-43998), a method of adding some kind of metal ion (JP Patent Publication (Kokai) No. 61-162193, JP Patent Publication (Kokoku) No. 6-55148, and JP Patent Publication (Kokai) No. 8-187092), or the like.

In contrast, a biocatalyst has low stability with regard to heat, and thus, reactions must be carried out at low temperatures. This results in a decreased reaction speed per catalyst. When producing a compound using a biocatalyst at the industrial level, therefore, the catalyst concentration in the reaction tank should be raised.

A currently known industrial process for producing an amide compound from a nitrile compound using a biocatalyst is similarly carried out by immobilizing microbial cells to make them particulate, raising the catalyst concentration in the reaction tank, and facilitating catalyst separation (see Kagaku to Kogyo (Chemistry and Chemical Industry) Vol. 43, No. 7, p. 1098-1101 (1990), JP Patent Publication (Kokai) Nos. 54-143593 and 54-144889). Also, a method for immobilizing the cell is studied (see JP Patent Publication (Kokai) Nos. 57-39792 and 62-294083). When effective production of an amide compound at the industrial level is intended, immobilization of cells at a higher concentration has been considered to be important (see JP Patent Publication (Kokai) No. 7-203964).

However, the present inventors entrap-immobilized a microbial cell that exhibits high nitrile hydratase activity and used it in the reaction. As a result, it was confirmed that a nitrile compound as a reaction substrate and/or an amide compound as a reaction product caused diffusion defects in the entrap-immobilized particles, and the reaction speed was significantly decreased.

For example, according to the comparison of initial reaction speeds between the entrap-immobilized cell and the unimmobilized cell, the reaction speed was significantly decreased to one-tenth or lower, depending on reaction conditions. Not only the initial reaction speed is significantly decreased, but also the activity of the enzyme in the entrap-immobilized catalyst, which does not fully contribute to the reaction due to diffusion defect, is lowered during the reaction. This also lowers the amount of amide compound produced per unit cell amount.

Specifically, decreased reaction speed or lowered amount of amide compound produced per unit cell amount as mentioned above results in unfavorable conditions. Under such conditions, it takes a long time to accumulate the targeted amount when producing an amide compound by a batch reaction, and the size of facilities must be enlarged in the case of a continuous reaction.

Accordingly, an object of the present invention is to solve problems occurring in the process for producing an amide compound from a nitrile compound using a biocatalyst, such as decreased reaction speed or lowered amount of amide compound produced per unit cell amount. These problems are caused by the use of immobilized microbial cell with highly exhibited nitrile hydratase activity.

In order to attain the above object, the present inventors have conducted concentrated studies concerning a more suitable form of catalyst than the immobilized catalyst. As a result, they have found that an amide compound could be more effectively produced when using a microbial cell that exhibits high nitrile hydratase activity of 50 U or higher per mg of dry cell at 10° C., and bringing the microbial cell into contact with a nitrite compound while suspended in an aqueous medium, than is the case when immobilizing the cell. This has led to the completion of the present invention.

More specifically, the present invention relates to a process for producing an amide compound from a nitrile compound using a microbial catalyst, wherein a microbial cell having nitrile hydratase activity of 50 U or higher per mg of dry cell at a reaction temperature of 10° C. is brought into contact with a nitrile compound in an aqueous medium without being immobilized.

DISCLOSURE OF THE INVENTION

The present invention is hereafter described in detail.

In the present invention, any microorganisms may be used as long as they have nitrile hydratase activity of 50 U or higher per mg of dry cell at a reaction temperature of 10° C. Examples of preferable microorganisms include those belonging to the genera *Bacillus, Bacteridium, Micrococcus, Brevibacterium* (JP Patent Publication (Kokoku) No. 62-21519), *Corynebacterium, Nocardia* (JP Patent Publication (Kokoku) No. 56-17918), *Pseudomonas* (JP Patent Publication (Kokoku) No. 59-37951), *Microbacterium* (JP Patent Publication (Kokoku) No. 4-4873), *Rhodococcus* (JP Patent Publication (Kokoku) Nos. 4-4873, 6-55148, and 7-40948), *Achromobacter* (JP Patent Publication (Kokai) No. 6-225780), and *Pseudonocardia* (JP Patent Publication (Kokai) No. 9-275978). Bacteria of the genus *Rhodococcus* are more preferable.

Alternatively, a transformant may be used. This is prepared by obtaining the aforementioned microorganism-derived nitrile hydratase gene and introducing the gene as such, or an artificially modified form thereof, into an arbitrary host.

Examples of the transformants include *E. coli* MT 10770 (FERM P-14756) transformed with a nitrile hydratase of the genus *Achromobacter* (JP Patent Publication (Kokai) No. 8-266277), *E. coli* MT 10822 (FERM BP-5785) transformed with a nitrile hydratase of the genus *Pseudonocardia* (JP Patent Publication (Kokai) No. 9-275978), or a microorganism transformed with a nitrile hydratase of the genus *Rhodococcus rhodochrous* (JP Patent Publication (Kokai) No. 4-211379).

The unit "U" of enzyme activity used in the present invention means that 1 μmol of corresponding amide compound is generated from a nitrile compound per minute. The term "enzyme activity" used herein refers to the value of enzyme activity measured utilizing a nitrile compound that is used in production.

The enzyme activity is measured by placing 5 mL of 50 mM phosphate buffer adjusted to the optimal pH (e.g., pH 7) of the enzyme in a test tube having a diameter of 30 mm, suspending 2 mg of the cultured and washed cells (dry weight) therein, and shaking the tube in a water tank at 10° C. About 5 minutes later, a phosphate buffer prepared in advance containing 1 to 5% of nitrile compound, placed at 10° C. and adjusted to the optimal pH, is added. The concentration of the amide compound generated after an arbitrary reaction time is measured using analyzing equipment such as gas chromatography or liquid chromatography, thereby calculating the enzyme activity.

The reaction time is determined in such a manner that a reaction solution retains a nitrile compound of a concentration at which the reaction speed is not decreased, and the concentration of the amide compound generated is high enough to be accurately measured at the end of the reaction.

The present invention is effective when a microbial cell having enzyme activity of 50 U or higher per mg of dry cell at 10° C. is used. It is more effective with the use of a microbial cell having enzyme activity of 80 U or higher, and even more effective with activity of 100 U or higher.

The nitrile compound according to the present invention is converted into a corresponding amide compound through the action of a nitrile hydratase. Examples thereof include: aliphatic saturated nitriles as exemplified by acetonitrile, propionitrile, succinonitrile, and adiponitrile; aliphatic unsaturated nitriles as exemplified by acrylonitrile and methacrylonitrile; aromatic nitriles as exemplified by benzonitrile and phthalodinitrile; and heterocyclic nitriles as exemplified by 3-cyanopyridine and 2-cyanopyridine. Because of the chemical and physical properties of a nitrile compound, the substrate specificity of a nitrile hydratase enzyme, and the industrial point of view, acrylonitrile and cyanopyridine are preferable as target compounds of the present invention.

In the present invention, a form of catalyst without being entrap-immobilized is such that a membrane of a microbial cell is in a direct contact with a reaction solution. An example thereof is a form of catalyst treated in an entrap-immobilization method in which a cell is not entrapped with high molecular substances such as polyacrylamide, polyvinyl alcohol, carrageenan, agar, gelatin, or alginic acid.

More specifically, the "catalyst without being entrap-immobilized" according to the present invention is a microbial cell itself that was cultured and optionally subjected to washing or other forms of treatment, a microbial cell that was chemically treated with a substance having a polyfunctional group such as glutaraldehyde, or a microbial cell that was chemically bonded onto a surface of a glass bead, resin, silica gel, or the like.

The use of a cell chemically treated with glutaraldehyde as a catalyst is particularly preferable from the viewpoint of improvement in the stability of catalyst enzyme activity.

The operation that brings a microbial cell into contact with a nitrile compound in an aqueous medium refers to one in which a microbial cell having nitrile hydratase activity is brought into contact with a nitrile compound in water or in an aqueous medium prepared by dissolving, for example, a stabilizer for ion strength, pH buffer capacity, or nitrile hydratase activity in water. This may be carried out by a batch system or a continuous system. A form of reaction is selected depending on properties of reaction substrate, reaction solution, target compound, and the like, or scale of production, and a reaction apparatus is designed based thereon.

Preferably, reaction conditions such as reaction temperature and pH are controlled to be optimal so that an amide compound can be produced on a smaller scale or within a shorter time.

The concentration of the amide compound accumulated by the above method is preferably 20% or higher, and more preferably 50% or higher, from an industrial point of view.

This description includes part or all of the content as disclosed in the description of Japanese Patent Application No. 2000-387537, which is a priority document of the present application.

BEST MODES FOR CARRYING OUT THE INVENTION

The present invention is hereafter described in more detail with reference to the following examples, although it is not limited thereto. In the following examples, "%" is by mass unless otherwise specified.

Example 1

Production of Acrylamide Using a Microbial Cell in an Aqueous Medium (1) Culture of Cell (i) Conditions for Preculture:

(Composition of Medium)

2% fructose, 5% polypeptone (Nihon Pharmaceutical Co., Ltd.), 0.3% yeast extract (Oriental Yeast Co., Ltd.), 0.1% $KH_2PO_4$, 0.1% $K_2HPO_4$, 0.1% $MgSO_4.7H_2O$, pH 7

(Culture Method)

A medium (100 ml) was fractionated into a 500 ml conical flask, the flask was cotton plugged, and it was then sterilized in an autoclave at 121° C. for 20 minutes. *Rhodococcus rhodochrous* J1 (FERM BP-1478) was inoculated and subjected to shake culture at 30° C. for 48 hours.

(ii) Conditions for Main Culture:

(Composition of Medium)

Initial medium: 0.2% yeast extract, 0.1% $KH_2PO_4$, 0.1% $K_2HPO_4$, 0.1% $MgSO_4.7H_2O$, 0.002% $CoCl_2.6H_2O$, 0.025% ammonium sulfate, 2% fructose, 2% urea, 0.4% ethanol, 0.1% Pluronic L61 (Asahi Denka Co., Ltd.), pH 7
Medium added later: 20% fructose, 5% ethanol, 6% ammonium sulfate, pH 6.5

(Culture Method)

The initial medium (2 liters) was fractionated into a 3-liter mini-jar fermenter and sterilized in an autoclave at 121° C. for 20 minutes. Separately, fructose, ethanol, and urea were aseptically filtered using a 0.45 micron filter paper (Advantec Toyo Kaisha, Ltd.) and added to the medium.

Culture was conducted under conditions at a pressure inside the tank of 0.098 MPa, an agitation rate of 600 rpm, an air-flow rate of 1 vvm, a pH of 7, and a temperature of 30° C. Culture was terminated when the maximal enzyme activity occurred. Thereafter, the culture product was washed with a 50 mM phosphate buffer (pH 7.7), and a suspension of cell (weight of dry cell: 15%) was obtained.

(2) Measurement of Nitrile Hydratase Activity

A 50 mM phosphate buffer (4.98 ml, pH 7.7) and 20 μL of suspension of cell were added and mixed in a test tube having a diameter of 30 mm, and the tube was shaken in a tank at 10° C. for 5 minutes. A 50 mM phosphate buffer (5 mL, pH 7.7) containing 5.0% acrylonitrile, which was previously set at 10° C., was added thereto, the product was allowed to react for 10 minutes, the cells were separated by filtration, and acrylamide generated was quantified by gas chromatography (GC-14B, SHIMADZU CORPORATION). Analysis was conducted using a 1 m glass column filled with Parabox PS (a column filler, Waters) at a column temperature of 230° C., and the FID detection was conducted at 250° C. The result indicated that 1.2% of acrylamide was generated. When "1 U" is defined as an amount of activity resulting when 1 micromole of acrylonitrile is converted into acrylamide at a reaction temperature of 10° C. within a reaction time of 1 minute, the activity of the cell for converting acrylonitrile into acrylamide was 56 U per mg of dry cell at 10° C.

(3) Conversion of Acrylonitrile into Acrylamide

A 50 mM TRIS (2-amino-2-hydroxymethyl-1,3-propanediol) hydrochloride buffer (664 g, pH 7.7) was placed in a 1 liter-jacketed separable flask. The suspension of cell obtained above was added thereto so as to bring the weight of dry cell to 90 mg. Acrylonitrile was continuously added thereto in order to maintain the acrylonitrile concentration at 2% at an agitation rate of 180 rpm at 18° C.

As a result, the concentration of the acrylamide, which was produced 25 hours after the initiation of acrylonitrile addition, reached the target level of 45%.

Comparative Example 1

Production of Acrylamide Using an Entrap-Immobilized Microbial Cell (1) Immobilization of Cells The suspension of cell obtained in Example 1 having activity of 56 U in terms of converting acrylonitrile into acrylamide was added to an equivalent amount of an aqueous solution of thoroughly dissolved 3% sodium alginate (Kanto Kagaku), and they were thoroughly mixed. This mixture was added dropwise to an aqueous solution of 1M calcium chloride through a silicon tube having an inner diameter of 2 mm. Thus, particles of immobilized cell having particle diameters of about 3 mm were obtained. The particles of immobilized cell were washed with a 50 mM TRIS hydrochloride buffer (adjusted to pH 7.7) to obtain immobilized cells.

(2) Conversion of Acrylonitrile into Acrylamide

A 50 mM TRIS hydrochloride buffer (664 g, pH 7.7) was placed in a 1 liter-jacketed separable flask. The immobilized cells obtained above were added thereto so as to bring the weight of dry cell to 90 mg. Acrylonitrile was continuously added thereto in order to maintain the acrylonitrile concentration at 2% at an agitation rate of 180 rpm at 18° C.

As a result, the acrylamide concentration did not reach the target level of 45% even 50 hours after the initiation of acrylonitrile addition.

Example 2

Production of Acrylamide Using Microbial Cell in an Aqueous Medium (1) Culture of Cell

*Pseudomonas chlororaphis* B23 (FERM BP-187) cell was cultured in the manner as described in the Example of JP Patent Publication (Kokai) No. 2-177883. The activity of this cell for converting acrylonitrile into acrylamide was measured in the same manner as in Example 1 at pH 7.7. As a result, the activity was 90 U per mg of dry cell at 10° C.

(2) Conversion of Acrylonitrile into Acrylamide

A 50 mM phosphate buffer (850 mL, pH 7.7) and 0.4 g of cell (on a dry basis) were added to a jacketed separable flask (internal volume: 1 liter). The reaction was carried out by continuously adding acrylonitrile while stirring at 3° C. to maintain the acrylonitrile concentration at 2%.

The acrylamide concentration reached the target level of 20% three hours later.

Comparative Example 2

Production of Acrylamide using Entrap-Immobilized Microbial Cell (1) Entrap-Immobilization of Cell An aqueous solution of monomer mixture was prepared so as to comprise 30%, 1%, and 4% of acrylamide, methylenebisacrylamide, and 2-dimethylaminopropyl methacrylamide, respectively.

Subsequently, the suspension of cell having activity of 90 U in terms of converting acrylonitrile into acrylamide obtained in Example 2, an aqueous monomer solution, an aqueous solution of 10% N,N,N',N'-tetramethyl ethylene diamine, and an aqueous solution of 10% ammonium persulfate were subjected to line-mixing at a mixing ratio of 50:20: 1:1. The effluents were successively placed on a bat having a size of 300×300×30 mm and then polymerized thereon.

The produced cell-immobilized gel sheet was cut into small pieces of about 0.5 $mm^2$ using a knife to obtain particles of acrylamide polymer entrap-immobilized cell. The particles of immobilized cell were washed by dipping in an aqueous solution of 0.1% sodium acrylate (adjusted to pH 7 with the aid of sodium hydroxide) for preparation.

(2) Conversion of Acrylonitrile into Acrylamide

Acrylonitrile was converted into acrylamide using the method and the apparatus as described in Example 2.

The acrylamide concentration did not reach the target level of 20% eight hours later.

Comparative Example 3

Production of Acrylamide using a Microbial Cell Having Low Nitrile Hydratase Activity (1) Culture of Cell and Preparation of Catalyst In the same manner as in Example 1, the *Rhodococcus rhodochrous* J1 (FERM BP-1478) cell was cultured. When the activity of the cell for converting acrylonitrile into acrylamide, which was measured based on the method for measuring activity as described in Example 1, reached 20 U per mg of dry cell at 10° C., culture was terminated. Thereafter, the culture product was washed with a 50 mM phosphate buffer (pH 7.7), and a suspension of cell (weight of dry cell: 15%) was obtained.

(2) Conversion of Acrylonitrile into Acrylamide

In accordance with the method described in Comparative Example 2, a suspension of acrylamide polymer entrap-immobilized cell was first prepared.

Subsequently, the aforementioned suspension of immobilized cell or suspension of unimmobilized cell was used as a microorganism in an amount of 225 mg in terms of the weight of dry cell, thereby converting acrylonitrile into acrylyamide. As a result, the acrylamide concentration reached the target level of 45% about 100 hours later with the use of a suspension of either immobilized or unimmobilized cells.

Specifically, there was no significant difference between immobilized cells and unimmobilized cells when the cell exhibited activity of 20 U.

All publications, patents, and patent applications cited herein are incorporated herein by reference in their entirety.

INDUSTRIAL APPLICABILITY

In the method according to the present invention, a microbial cell that exhibits high nitrile hydratase activity is used in the reaction without being entrap-immobilized. Thus, an amide compound can be effectively produced from a nitrile compound without problems of decreased reaction speed or lower amount produced per unit cell amount, which are caused by entrap-immobilization. Accordingly, an amide compound can be produced within a very short period of time in the case of a batch reaction and with a very small-scale facility in the case of a continuous reaction.

What is claimed is:

1. A process for producing an amide compound from a nitrile compound comprising:

contacting an aqueous medium of acrylonitrile or cyanopyridine with a suspension of microbial cells having nitrile hydratase activity of at least 50 U per mg of dry cell measured at a reaction temperature of 10° C. for a time and under conditions suitable for conversion of acrylonitrile or cyanopyridine into its corresponding amide compound, continuously adding the acrylonitrile or cyanopyridine to the aqueous medium, and obtaining a concentration of at least 20% of the amide compound in the aqueous medium;

wherein said microbial cells having nitrile hydratase activity are at least one of *Rhodococcus rhodochrous* J1 (FERM BP-1478) and *Pseudomonas chlororaphis* B23 (FERM BP-187).

2. A process for producing an aliphatic saturated amide, an aromatic amide, or a heterocyclic amide from a substrate that is an aliphatic saturated nitrile, an aromatic nitrile, or a heterocyclic nitrile, respectively, comprising:

contacting a suspension of microbial cells having nitrile hydratase activity of at least 50 U per mg of dry cell measured at a reaction temperature of 10° C. with an aqueous reaction solution containing an aliphatic saturated nitrile, an aromatic nitrile, or a heterocyclic nitrile for a time and under conditions suitable for the production of aliphatic saturated amide, an aromatic amide, or a heterocyclic amide, continuously adding the aliphatic saturated nitrile, an aromatic nitrile, or a heterocyclic nitrile to the aqueous reaction solution, and recovering a concentration of at least 20% of the aliphatic saturated amide, the aromatic amide, or the heterocyclic amide in the aqueous reaction solution, wherein said microbial cells having nitrile hydratase activity are at least one of *Rhodococcus rhodochrous* J1 (FERM BP-1478) and *Pseudomonas chlororaphis* B23 (FERM BP-187).

3. The process of claim 2, wherein said substrate is acrylonitrile.

4. The process of claim 2, wherein said substrate is cyanopyridine.

* * * * *